United States Patent [19]

Beskin

[11] 4,316,473

[45] Feb. 23, 1982

[54] PORTABLE BLOOD SAMPLE TEMPERATURE CONTROL SYSTEM

[75] Inventor: Gerald S. Beskin, Minneapolis, Minn.

[73] Assignee: Therapac Division, Krelitz Industries, Inc., Minneapolis, Minn.

[21] Appl. No.: 141,423

[22] Filed: Apr. 18, 1980

[51] Int. Cl.³ .................... A61B 5/14

[52] U.S. Cl. .................... 128/763; 62/457; 128/218 R; 165/80 E; 165/154; 222/146 C

[58] Field of Search .................... 128/218 R, 763, 760; 165/80 E, 154; 62/457, 530; 222/130, 131, 146 C, 146 R

[56] References Cited

U.S. PATENT DOCUMENTS

| | | | |
|---|---|---|---|
| 905,439 | 12/1908 | Kruger | 165/80 E |
| 1,771,186 | 7/1930 | Mock | 62/457 |
| 1,851,794 | 3/1932 | Wilson | 222/131 |
| 2,076,903 | 4/1937 | Levitt | 165/80 E |
| 2,564,165 | 8/1951 | Magis | 62/457 |
| 4,183,226 | 1/1980 | Moore | 62/457 |

*Primary Examiner*—Kyle L. Howell

*Attorney, Agent, or Firm*—Schroeder, Siegfried, Vidas, Steffey & Arrett

[57] ABSTRACT

A temperature control system for a syringe contained blood sample. Specifically, the system reduces the temperature of the blood sample to reduce the volatility of the blood gases. A first cylindrical member defines a chamber, the chamber accepting a blood sample containing syringe through an end thereof. A second, concentric cylindrical member cooperates with the first cylindrical member to define a reservoir surrounding the chamber. A heat sink material within the reservoir withdraws heat from the chamber to reduce the temperature of a blood sample within the chamber. In a preferred embodiment, the first and second cylindrical members are formed as integral structures having an end wall extending therebetween. A cap, which may be self-sealing with the two cylindrical members, forms an opposing end wall. Either end wall may function as a support to establish a desired chamber orientation. In a preferred embodiment, the cap provides the chamber support and is provided with flanges, which, selectively, stabilize the chamber such that its axis is either substantially vertical or slightly skewed from horizontal. When the unitary end wall supports the chamber, the cap may serve to center a blood sample containing syringe within the chamber.

9 Claims, 6 Drawing Figures

PORTABLE BLOOD SAMPLE TEMPERATURE CONTROL SYSTEM

BACKGROUND OF THE INVENTION

Blood gas volatility poses well-known problems in the usual circumstances wherein a blood sample is taken at one location and transported for blood gas tests at a remote laboratory. It is also known that the volatility of gases in the blood can be reduced by lowering the temperature of the blood sample. In the past, blood gas volatility reduction has been accomplished in a haphazard manner as by placing a syringe contained blood sample on or within crushed ice. While a preferred practice may be to position the syringe within the ice, the common practice is to place the syringe on the ice. Clearly, this results in a less than optimum cooling of a blood sample and, accordingly, a less than optimum decrease in the volatility of the gases in the blood and maintaining of the integrity of its gas content. Further, the use of crushed ice requires some type of container or tray for the ice which contributes unnecessarily to bulk during transportation and produces an objectionable wetness in the laboratory.

SUMMARY OF THE INVENTION

The present invention provides a highly compact and portable temperature control system for a syringe contained blood sample and includes a chamber for accepting a blood sample containing syringe and a reservoir surrounding the chamber, the reservoir containing a heat sink material for withdrawing heat from the chamber. A first cylindrical member defines the chamber while a second, concentric cylindrical member, in cooperation with the first cylindrical member, defines the reservoir. Preferably, the cylindrical members are formed as a unitary structure with an end wall extending therebetween. Another end wall may be formed by a cap, which, in a preferred embodiment, is self-sealing with both the first and second cylinders to insure the integrity of the reservoir. The chamber may be supported with the axis of the first cylinder being generally vertical on either the unitary end wall or the cap. When supported on the unitary end wall, provision may be made in the cap to facilitate the centering of a blood sample containing syringe within the chamber. Alternatively, the cap may be provided with flanges to further stabilize the chamber when the first member axis is in the vertical orientation or to establish and maintain that axis in an orientation slightly skewed from horizontal. In all cases, the chamber is at least coextensive with the contained blood sample with the heat sink material containing reservoir completely surrounding that chamber to enhance the uniformity of the heat transfer from the blood sample.

DETAILED DESCRIPTION OF THE DRAWINGS

Figure 1:
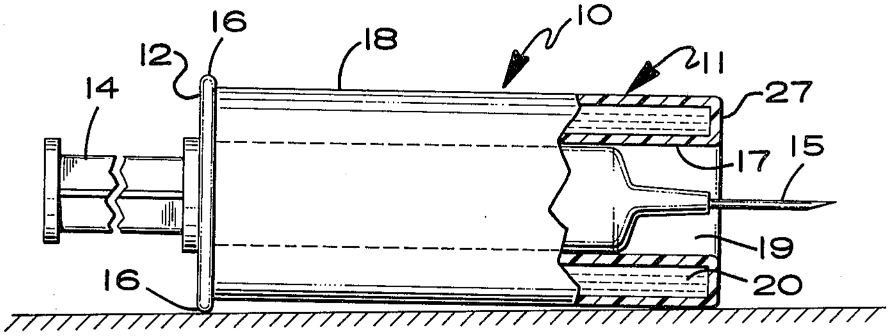
FIG. 1 illustrates a side view of a preferred embodiment of the present invention.

Referring now to FIG. 1, there is illustrated a preferred embodiment of the present invention designated generally at 10 and including a body portion 11 and cooperating cap 12. As will be discussed more fully below, the body portion 11 has a central chamber surrounded by a reservoir, the reservoir containing a heat sink material. Access to the body portion 11 chamber, in the embodiment illustrated in FIG. 1, may be obtained through either end as by a central aperture 13 in cap 12 (see FIG. 2) which aperture opens into the chamber of body portion 11. The chamber is adapted to receive a syringe which has been employed to take a blood sample with the heat sink material in the reservoir surrounding the chamber serving to cool the blood sample and reduce the blood gas volatility thereof. This is illustrated within the chamber in FIG. 1 with the syringe plunger 14 extending away from the cap 12 and the syringe needle 15 extending out from the chamber in body portion 11 from the opposite end thereof. That portion of the syringe containing the blood sample is contained within the chamber with the chamber being at least coextensive with the blood sample contained in the syringe. As illustrated in FIG. 1, the cap 12 extends from the side wall of the body portion 11 so as to maintain the axis of the body portion 11 slightly skewed from horizontal. This angular orientation assists in maintaining the syringe within the chamber in the body portion 11.

Figure 2:
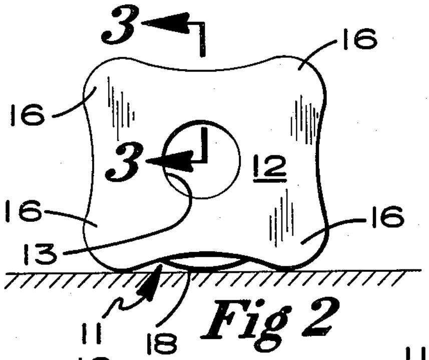
FIG. 2 illustrates an end view of the preferred embodiment of FIG. 1.

FIG. 2 illustrates an end view of the preferred embodiment of FIG. 1 including cap 12 and central aperture 13 as well as a portion of the body portion 11, which is visible in FIG. 2 as a result of its skewed orientation. Cap 12 is provided with flanges 16 which stabilize the unit when it is in the nearly horizontal orientation illustrated in FIG. 1. That is, the outer surface of the body portion 11 is generally cylindrical. However, the flanges on cap 12, in addition to skewing the body portion 11 from horizontal, prevent the body portion 11 from rolling.

Figure 3:
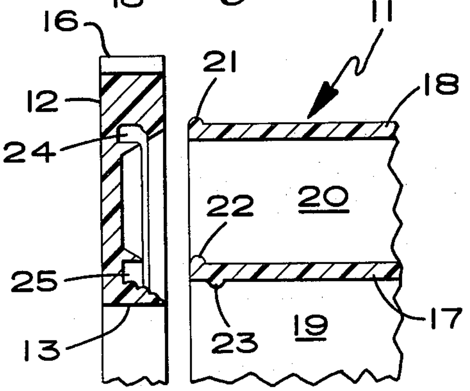
FIG. 3 is an enlarged view taken along the line 3—3 in FIG. 2.

FIG. 3 is an enlarged view taken along the line 3—3 in FIG. 2, which illustrates the cooperation between the body portion 11 and the cap 12 to provide a seal within the reservoir surrounding the chamber of body portion 11. As illustrated in FIG. 3, body portion 11 is formed of an inner-cylindrical wall 17 and an outer cylindrical wall 18 which define a chamber 19 and a reservoir 20. The cap 12 cooperates with the walls 17 and 18 to provide a seal of the reservoir 20 at one end with another end wall providing a seal at the other end of the walls 17 and 18, as will be described more fully below. A bead 21 is provided on the outer surface of the wall 18 while beads 22 and 23 are provided on the wall 17. A recess 24 in cap 12 cooperates with the bead 21 and the wall 18 to provide a seal at the wall 18 while a recess 25 cooperates with the beads 22 and 23 to provide a seal at wall 17. The seal may be enhanced by a selection of the materials forming the body portion 11 and cap 12. In a preferred embodiment, the body portion will be formed of a high impact polystyrene while the cap will be formed of polyethylene, the resiliency of the polyethylene enhancing the seal of the reservoir 20.

Figure 4:
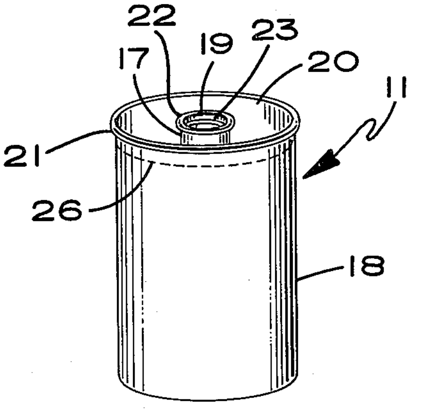
FIG. 4 illustrates a portion of a preferred embodiment of FIG. 1.

FIG. 4 illustrates the manner in which the temperature control system of the present invention is assembled. The body portion 11 is first placed on the unitary end wall opposite the end of body portion 11 which cooperates with the cap 12. In this orientation, both the chamber 19 and reservoir 20 are exposed. The reservoir 20 is then filled with a heat sink material after which the cap is positioned to seal the reservoir. The cap may employ seals of the type described with reference to FIG. 3, or alternatively, may be adhesively or heat secured and sealed to the ends of the walls 17 and 18. The heat sink material may be water, but is preferably a water base propylene glycol to reduce the freezing temperature. When a material that expands on freezing is employed, expansion room must be left as by filling the reservoir 20 to the height of the dotted line 26 in FIG. 4. With the described propylene glycol heat sink material, an expansion space of approximately four percent of total reservoir volume is sufficient.

Figure 5:
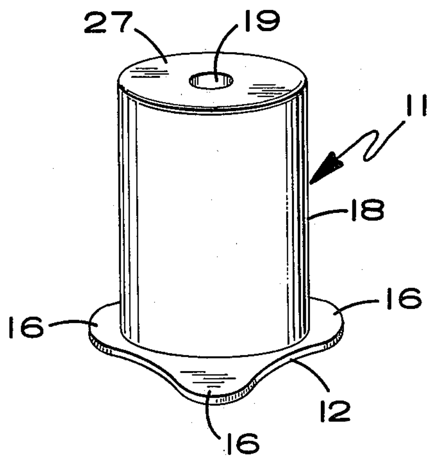
FIG. 5 illustrates an alternative orientation of the preferred embodiment of FIG. 1.

With the heat sink material in place and the cap secured to the walls 17 and 18, the temperature control system of the present invention is placed in a sub-freezing temperature as by placing it in a freezer. Preferably, the heat sink material is frozen while the system is in a vertical position so as to assure that the heat sink material surrounds the chamber 19. Once frozen, the system is ready for use as illustrated in FIG. 1. FIG. 5 illustrates an alternative orientation of the system of the present invention with the axis of the chamber being substantially vertical and with cover 12 serving as a base. The flanges 16 of the cover 12 also provide stability to the system in the orientation illustrated in FIG. 5. FIG. 5 also provides a view of the unitary end wall 27 extending between the cylindrical walls 17 and 18. In the orientation illustrated in FIG. 5, in order to avoid excessive height while fully accommodating the blood sample, it will be desirable to remove the needle 15 from the syringe. Caps to avoid blood sample leakage after needle removal are known to the prior art. As an additional alternative, the system of the present invention may be supported on the end wall 27 with the central aperture 13 in the cap 12 serving to center the syringe within the chamber 19.

Figure 6:
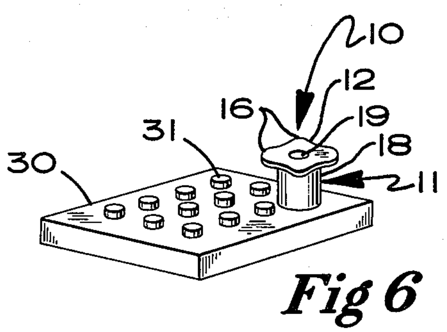
FIG. 6 illustrates a preferred packaging system for the preferred embodiment of FIGS. 1 through 5.

In use, the units are placed within a freezer in the vertical orientation to freeze the heat sink material. A packaging system to facilitate this operation is illustrated in FIG. 6 wherein a base 30 is provided with a plurality of upstanding pegs 31. Pegs 31 are of a size which will fit within the chamber 19 and provide sufficient engagement with the chamber 19 to maintain a reservoir 20, and chamber 19, in a vertical orientation as illustrated in FIG. 6. Further pegs 31 block entry of foreign matter into the chamber from one end thereof. Plugs may be employed in the other end for the same purpose.

Obviously, many modifications and variations of the present invention are possible in light of the above teachings. For example, the cap 12 may be provided with a different configuration without departing from the scope of the present invention. As already noted, the cap 12 and body portion 11 may be secured to each other in a manner other than that illustrated in FIG. 3. It is therefore to be understood that, within the scope of the appended claims, the invention may be practiced otherwise than is specifically described.

I claim:

1. A portable temperature control system which comprises:

a syringe containing a blood sample, first wall means defining a chamber having access means for accepting said blood sample containing syringe, said chamber being at least coextensive with said contained blood sample;

second wall means cooperating with said first wall means for defining reservoir means surrounding said chamber;

heat sink means within said reservoir means for uniformly withdrawing heat from said chamber; and support means extending from said second wall means for selectively orienting said chamber.

2. The temperature control system of claim 1 wherein said first and second wall means comprise generally concentric cylindrical means.

3. The temperature control system of claim 2 wherein said support means comprises means for selectively maintaining said chamber in either of two distinct orientations.

4. The temperature control system of claim 3 wherein said distinct orientations comprise a first orientation wherein the axes of said cylindrical means are substantially vertical and a second orientation wherein said axes are slightly skewed from horizontal.

5. The temperature control system of claim 2 wherein said first and second cylindrical means are spaced from each other and are formed as a unitary structure including an end wall extending therebetween, said support means comprising cap means cooperating with said first and second cylindrical means and forming another end wall extending therebetween.

6. The temperature control system of claim 5 wherein said cap means further comprises flange means for stabilizing said chamber in either of two distinct orientations.

7. The temperature control system of claim 6 wherein said distinct orientations comprise a first orientation wherein the axes of said cylindrical means are substantially vertical and a second orientation wherein said axes are slightly skewed from horizontal.

8. The temperature control system of claim 5 wherein said unitary end wall forms said support means, said cap means further comprising means for facilitating the centering of a blood sample containing syringe within said chamber.

9. The temperature control system of claim 8 wherein said cap means and said first and second wall means comprise reservoir means self-sealing means.

* * * * *